United States Patent [19]

Karrer

[11] 4,294,949

[45] Oct. 13, 1981

[54] NOVEL POLYMERIC COMPOUNDS

[75] Inventor: Friedrich Karrer, Zofingen, Switzerland

[73] Assignee: Ciba-Geigy Corporation, Ardsley, N.Y.

[21] Appl. No.: 115,277

[22] Filed: Jan. 25, 1980

Related U.S. Application Data

[63] Continuation-in-part of Ser. No. 924,417, Jul. 13, 1978, Pat. No. 4,210,612.

[30] Foreign Application Priority Data

Jul. 19, 1977 [CH]   Switzerland ......................... 8915/77

[51] Int. Cl.$^3$ ............................................ C08F 226/06
[52] U.S. Cl. ............................... 526/262; 204/159.22; 526/258; 526/263; 526/265
[58] Field of Search ................... 204/159.22; 526/263, 526/265, 258, 262

[56] References Cited

U.S. PATENT DOCUMENTS

| | | | |
|---|---|---|---|
| 3,004,957 | 10/1961 | Lynn | 526/265 |
| 3,645,988 | 2/1972 | Hammet et al. | 526/265 |
| 4,210,612 | 7/1980 | Karrer | 526/263 |

*Primary Examiner*—Harry Wong, Jr.
*Attorney, Agent, or Firm*—Wenderoth, Lind & Ponack

[57] ABSTRACT

Homopolymeric acrylates and methacrylates which carry N-heterocyclic rings in a side position and their copolymers with compounds containing at least one polymerizable double bond are suitable as additives for plastics.

12 Claims, No Drawings

NOVEL POLYMERIC COMPOUNDS

This is a continuation-in-part Application of the copending Application Ser. No. 924,417 filed July 13, 1978 (now U.S. Pat. No. 4,210,612).

The present invention relates to organic material containing homopolymeric and copolymeric compounds, the preparation of these compounds and their use as light stabilisers in organic material.

It is known from U.S. Pat. No. 3,705,166 to use monomeric acrylic acid derivatives which contain at least one piperidinyl group having a sterically hindered nitrogen atom as light stabilisers in organic polymers. However, these acrylic acid derivatives are too readily volatile. Furthermore, the possibility of incorporating the monomeric additive in certain substrates is pointed out. However, this has the disadvantage that the polymer structure is destroyed by the additive incorporated and this can lead to a change, which is difficult to regulate, in the characteristics of the substrate to be protected. In Japanese Published Specification No. 49-75,469 water-soluble polymeric acrylic acid and methacrylic acid derivatives have been proposed as flocculating agents.

Homopolymeric and copolymeric additives have now been found which, in addition to excellent light-stabilising properties, have good solubility or compatibility in the polymer and a high stability to extraction.

The present invention thus relates to organic material containing homopolymeric compounds which carry N-heterocyclic rings in a side position and have the recurring structural unit of the formula I $$\left[ \begin{array}{cc} R_1 & R_3 \\ | & | \\ C - C \\ | & | \\ R_2 & R_4 \end{array} \right] \quad (I)$$

in which $R_1$ is a group, containing an N-heterocyclic ring, of the formulae II, III, IV and V

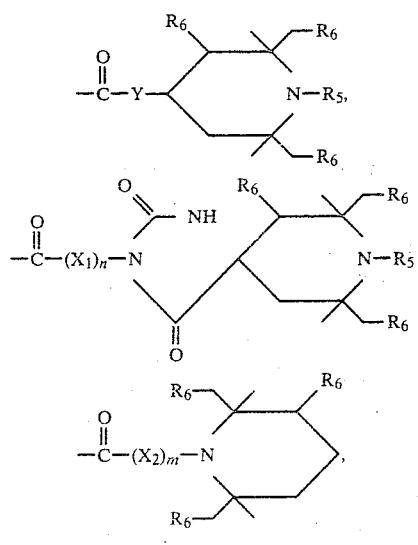

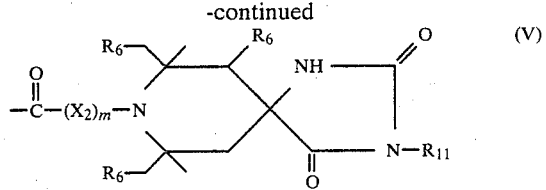

in which $R_5$ is hydrogen, oxyl, $C_1$-$C_{18}$ alkyl, 2-hydroxyethyl, 2-hydroxypropyl, $C_3$-$C_8$ alkenyl, $C_3$-$C_6$ alkynyl, $C_7$-$C_{12}$ aralkyl, $C_2$-$C_{21}$ alkoxyalkyl, an aliphatic acyl group having 1-4 C atoms or one of the groups —CH$_2$COOR$_7$ or —COOR$_8$, in which $R_7$ is $C_1$-$C_{12}$ alkyl, $C_3$-$C_8$ alkenyl, phenyl, $C_7$-$C_8$ aralkyl or cyclohexyl and $R_8$ is $C_1$-$C_{12}$ alkyl, phenyl, benzyl or cyclohexyl, and $R_6$ is hydrogen or $C_1$-$C_4$ alkyl and Y is —O— or

in which $R_9$ is hydrogen, $C_1$-$C_{12}$ alkyl, $C_7$-$C_{12}$ aralkyl or cyclohexyl, and $X_1$ is a group of the formula —O—CH(R$_{10}$)—CH$_2$— (VI) or denotes —O—CH$_2$—CH$_2$—CH$_2$—, in which $R_{10}$ is hydrogen, methyl, ethyl, phenoxymethyl or phenyl, and n is 0 or 1, and $X_2$ is a group of the formula VI, in which $R_{10}$ is as defined above, or a group of the formula —O—CH$_2$—CH(OH)—CH$_2$— (VII), and m is 0 or 1, and $R_{11}$ is $C_1$-$C_{18}$ alkyl or is cyclohexyl, phenyl or benzyl which are unsubstituted or substituted by $C_1$-$C_4$ alkyl or $C_1$-$C_4$ alkoxy, and $R_2$ is hydrogen or $C_1$-$C_4$ alkyl, and, if $R_2$ and $R_4$ are hydrogen, $R_1$ and $R_3$ together form a group of the formula VIII

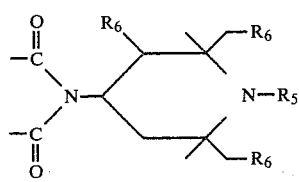

in which $R_5$ and $R_6$ are as defined above and $R_3$ is hydrogen or $C_1$-$C_2$ alkyl and $R_4$ is hydrogen or methyl, or their copolymers with compounds containing at least one polymerisable double bond, the molar ratio of the component of the formula I to the comonomer component being up to 1:10.

$R_1$ can be a group of the formulae II, III, IV or V. Preferably, $R_1$ is a group of the formulae II or IV.

As $C_1$-$C_4$ alkyl, $R_2$ is, for example, methyl, ethyl, n-propyl or n-butyl, especially ethyl, but in particular methyl, or $R_2$ is hydrogen.

As $C_1$-$C_2$ alkyl, $R_3$ is ethyl or especially methyl.

As $C_1$-$C_{18}$ alkyl, $R_5$ is, for example, methyl, ethyl, n-propyl, n-butyl, n-pentyl, n-octyl, n-decyl, n-dodecyl or octadecyl. Preferred alkyl groups are those having 1-12 C atoms, also those having 1-8 C atoms and especially those having 1-4 C atoms and in particular methyl.

As $C_3$-$C_8$ alkenyl, $R_5$ is, for example, allyl, 3-methyl-2-butenyl, 2-butenyl, 2-hexenyl or 2-octenyl, especially allyl.

As $C_3$-$C_6$ alkynyl, $R_5$ is, for example, propargyl.

As $C_7-C_{12}$ aralkyl, $R_5$ is, for example, benzyl, β-phenylethyl or 4-tert.-butyl-benzyl.

If $R_5$ is $C_2-C_{21}$ alkoxyalkyl, the alkyl part can contain 1–3 C atoms and the alkoxy part can consist of 1–18 C atoms, as, for example, in methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl; preferred compounds are those in which $R_5$ is an alkoxyalkyl group having 2–6 C atoms.

As an aliphatic acyl group having 1–4 C atoms, $R_5$ is, for example, formyl, acetyl, acryloyl or crotonoyl, especially acetyl.

As $C_1-C_4$ alkyl, $R_6$ is branched or, especially, non-branched alkyl, such as ethyl, n-propyl or n-butyl, but in particular methyl. $R_6$ is preferably hydrogen.

As $C_1-C_{12}$ alkyl, $R_9$ is, for example, methyl, ethyl, n-propyl, n-butyl, n-pentyl, n-octyl, n-decyl or n-dodecyl; preferably, however, $R_9$ is $C_1-C_4$ alkyl.

As $C_7-C_{12}$ aralkyl, $R_9$ is especially phenylethyl or in particular benzyl.

$R_{10}$ is phenyl or phenoxymethyl, preferably methyl or ethyl and especially hydrogen.

As $C_1-C_{18}$ alkyl, $R_{11}$ is, for example, methyl, ethyl, propyl, butyl, hexyl, octyl, dodecyl or octadecyl. Preferred alkyl groups are those having 1–12 C atoms.

$R_{11}$ can also be benzyl, cyclohexyl or phenyl and these can be substituted in the nucleus by $C_1-C_4$ alkyl, such as methyl, ethyl, propyl or n-butyl, or by $C_1-C_4$ alkoxy, such as methoxy, ethoxy, propoxy or n-butoxy.

If $R_5$ is the group $-CH_2COOR_7$ or $-COOR_8$, $R_7$ and $R_8$, as $C_1-C_{12}$ alkyl, are, for example, methyl, ethyl, isopropyl, n-butyl, isobutyl, t-butyl, isopentyl, n-octyl or n-dodecyl. Preferably, $R_7$ and $R_8$ are $C_1-C_4$ alkyl. As $C_3-C_8$ alkenyl, $R_7$ is, for example, allyl, 2-butenyl or 2-hexenyl. As $C_7-C_8$ aralkyl, $R_7$ is, for example, benzyl or α-phenylethyl. Y is $-O-$ or

preferably $-O-$.

The homopolymers characterised by the definition given above are good light stabilisers. Homopolymers with recurring structural unit of the formulae I, wherein $R_1$ denotes a group of the formulae III, IV and V, and the other symbols have the above meaning are novel and therefore a part of this invention. Nevertheless, in many cases it is advantageous to modify these homopolymers by copolymerisation with at least one compound which has one or more polymerisable double bonds. Such copolymers are novel and therefore a part of this invention. The characteristics, such as the solubility or the softening point, of the additive can be influenced in a simple manner by this means. Suitable copolymerisable components are, for example, styrene, divinylbenzene, 2- or 4-vinylpyridine or compounds of the acrylic acid series, such as esters or amides which are derived from acrylic acid or methacrylic acid, for example methyl acrylate, butyl acrylate, methyl methacrylate, acrylonitrile, methacrylonitrile, glycidyl acrylate, methylene-bisacrylamide or ethylene glycol dimethyl acrylate; alternatively, these components can be 1-alkenes having 2–10 C atoms, for example ethylene, propylene, 1-butene, 1-pentene, 1-hexene, 1-octene or 1-decene; furthermore, these components can be isoprene, butadiene, vinyl esters, such as vinyl acetate, or vinyl ethers, N-vinyl-2-pyrrolidone, N-vinyl-carbazole, maleimides or unsaturated phosphonates. Preferred copolymerisable components are styrene, acrylonitrile, acrylates or methacrylates, vinyl esters, vinyl ethers or acrylamides or methacrylamides.

Copolymers can also be prepared from two different piperidyl monomers. Such copolymers are also novel and a part of this invention. Compounds in which $R_1$ and $R_2$ together are a group of the formula VIII are especially suitable for copolymerisation reactions, either with other piperidinyl monomers or other above-mentioned polymerisable components.

The compound chosen specifically as the comonomer component plays a minor role, i.e. the compounds listed above are interchangeable to a considerable extent. The measures which have to be taken in order to obtain copolymers of similar molecular weight and similar properties are known to those skilled in the art. Of course, it is also possible to use copolymers obtained from more than two monomer components, for example terpolymers.

The molecular weight of the homopolymers and copolymers according to the invention is preferably more than 500; however it can by all means be up to 150,000. Preferred compounds have a molecular weight of 500 to 50,000 and especially of 1,000–20,000.

As already mentioned, the copolymerisable component can be omitted completely or can be used in an up to 10-fold excess. The molar ratio of the compound containing N-heterocyclic rings in a side position to the co-component is thus preferably about 1:0.001 to 1:10 and especially 1:0.01 to 1:5. This means, then, that the amount of the co-component can be very small (for example 1% relative to the component of the formula I). This will be the case especially when the co-component has two polymerisable double bonds, such as divinylbenzene or bis-acrylates or bis-methacrylates, with which branched or crosslinked additives are formed. In especially preferred copolymers the molar ratio of the compound containing N-heterocyclic rings in a side position to the co-component is 1:10 to 10:1.

Compounds to be singled out are homopolymeric compounds of the formula I in which $R_1$ is a group of the formulae II, III, IV or V, in which $R_5$ is hydrogen, $C_1-C_{12}$ alkyl, 2-hydroxyethyl, 2-hydroxypropyl, $C_3-C_5$ alkenyl, propargyl, $C_7-C_8$ aralkyl, acetyl or $C_2-C_{10}$ alkoxyalkyl and $R_6$ is hydrogen or methyl and Y is $-O-$ or

in which $R_9$ is hydrogen, $C_1-C_{12}$ alkyl or benzyl, and $X_1$ is a group of the formula VI or denotes $-O-CH_2-CH_2-CH_2-$, in which $R_{10}$ is hydrogen or methyl, and n is 0 or 1, and $X_2$ is a group of the formulae VI or VII, in which $R_{10}$ is as defined above, and m is 0 or 1, and $R_{11}$ is $C_1-C_{12}$ alkyl or benzyl, and $R_2$ is hydrogen or $C_1-C_2$ alkyl, or, if $R_2$ and $R_4$ are hydrogen, $R_1$ and $R_3$ together form a group of the formula VIII, in which $R_5$ and $R_6$ are as defined above, and $R_3$ is hydrogen or $C_1-C_2$ alkyl and $R_4$ is hydrogen or methyl, and their copolymers with compounds containing at least one polymerisable double bond.

Preferred compounds are homopolymeric compounds of the formula I in which $R_1$ is a group of the formulae II or IV, in which $R_5$ is hydrogen, $C_1-C_8$ alkyl, benzyl or acetyl and R₆ is hydrogen or methyl and Y is —O— or

in which R₉ is hydrogen or C₁–C₈ alkyl, and X₂ is a group of the formulae VI or VII, in which R₁₀ is hydrogen, methyl or ethyl, and m is 0 or 1, and R₂ is hydrogen or methyl or, if R₂ and R₄ are hydrogen, R₁ and R₃ together are a group of the formula VIII, in which R₅ and R₆ are as defined above, and R₃ is hydrogen or methyl and R₄ is hydrogen, and their copolymers with compounds containing at least one polymerisable double bond.

Further preferred compounds are homopolymeric compounds of the formula I in which R₁ is a group of the formulae II or IV, in which R₅ is hydrogen, C₁–C₄ alkyl, benzyl or acetyl and R₆ is hydrogen and Y is —O— or

in which R₉ is hydrogen or C₁–C₄ alkyl, and X₂ is a group of the formulae VI or VII, in which R₁₀ is hydrogen or methyl, and m is 0 or 1, and R₂ and R₃ independently of one another are hydrogen or methyl and R₄ is hydrogen, and their copolymers with styrene, acrylonitrile, an acrylate or a methacrylate, a vinyl ester, a vinyl ether or an acrylamide or methacrylamide.

Particularly preferred compounds are homopolymeric compounds of the formula I in which R₁ is a group of the formulae II or IV, in which R₅ is hydrogen, methyl or acetyl and R₆ is hydrogen and Y is —O— or

in which R₉ is hydrogen or C₁–C₄ alkyl, and X₂ is a group of the formulae VI or VII, in which R₁₀ is hydrogen, and m is 0 or 1, and R₃ and R₄ are hydrogen and R₂ is hydrogen or methyl, and their copolymers with styrene, acrylonitrile, an acrylate or methacrylate, a vinyl ester, a vinyl ether or an acrylamide or methacrylamide.

Examples of monomers which are suitable for polymerisation or copolymerisation to the polymers according to the invention are: 1-methacryloyloxyethyl-2,2,6,6-tetramethyl-piperidine, 1-acryloyloxyethyl-2,2,6,6-tetramethyl-piperidine, 1,2,2,6,6-pentamethyl-4-maleimido-piperidine, 1-acetyl-2,2,6,6-tetramethyl-4-maleimidopiperidine, 1-benzyl-2,2,6,6-tetramethyl-4-maleimidopiperidine, 1,3,8-triaza-2,4-dioxo-3-acryloyl-oxyethyl-7,7,8,9,9-pentamethyl-spiro[4,5]-decane, 1,3,8-triaza-2,4-dioxo-3-methacryloyl-oxyethyl-7,7,8,9,9-pentamethyl-spiro-[4,5]-decane, 1,3,8-triaza-2,4-dioxo-3-n-dodecyl-7,7,9,9-tetramethyl-8-methacryloyl-oxyethyl-spiro-[4,5]-decane, 1,3,8-triaza-2,4-dioxo-3-methacryloyl-oxyethyl-7,7,9,9-tetramethyl-8-benzyl-spiro-[4,5]-decane, 1,3,8-triaza-2,4-dioxo-3-n-butyl-7,7,9,9-tetramethyl-8-acryloyl-oxyethyl-spiro-[4,5]-decane, 1-benzyl-2,2,6,6-tetramethyl-4-(N-n-butyl)-methacrylamidopiperidine, 1,2,2,6,6-pentamethyl-4-(N-benzyl)-acrylamidopiperidine, 1,2,2,6,6-pentamethyl-4-(N-n-propyl)-acrylamidopiperidine, 1,2,2,6,6-pentamethyl-4-(N-n-propyl)-methacrylamido-piperidine, 1-allyl-2,2,6,6-tetramethyl-4-acryloyloxypiperidine, 1-allyl-2,2,6,6-tetramethyl-4-methacryloyloxypiperidine, 1,2,2,6,6-pentamethyl-4-acrylamido-piperidine, 1-benzyl-2,2,6,6-tetramethyl-4-(N-n-butyl)-acrylamido-piperidine, 1-benzyl-2,2,6,6-tetramethyl-4-acrylamido-piperidine and 1-[3'-acryloyloxy-(2'-hydroxy)-propyl]-2,2,6,6-tetramethylpiperidine.

The monomers which are suitable as starting materials for the polymerisation reaction are of the general formula IX

in which R₁, R₂, R₃ and R₄ are as defined above. With the exception of the compounds in which R₁ is a group of the formula II, in which Y is —O— or

and R₅ and R₆ are hydrogen, and R₂ and R₃ are hydrogen or methyl and R₄ is hydrogen, the monomers are novel and are therefore also a subject of the invention. In addition to the fact that they are useful as starting materials for the preparation of homopolymeric or copolymeric light stabilisers, the monomers of the formula IX are themselves light stabilisers for organic material.

The monomers of the formula IX employed for the polymerisation are prepared in a manner which is known per se, for example analogously to the methods described in U.S. Pat. No. 3,705,166. For this purpose, for example, a reactive derivative of an unsaturated carboxylic acid of the formula X

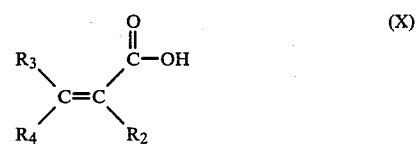

is reacted with one of the compounds of the formulae XI, XII, XIII or XIV

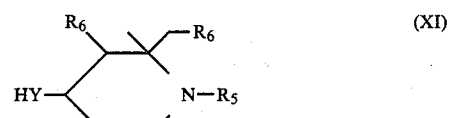

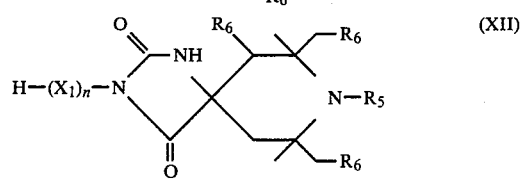

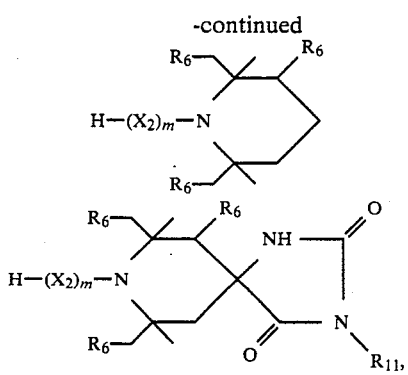 (XIII)

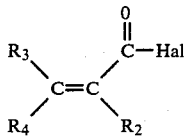 (XIV)

in which all of the substituents are as defined above, preferably in an inert organic solvent.

Reactive derivatives of an unsaturated carboxylic acid are, for example, an acid halide of the formula Xa

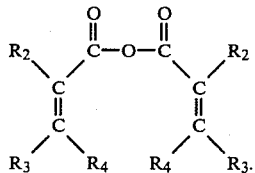 (Xa)

in which Hal is bromine or especially chlorine, or an acid anhydride of the formula Xb $$\underset{R_3}{\overset{R_2}{\diagdown}}C=C\underset{R_4}{\overset{\overset{O}{\|}}{\diagdown}}C-O-\overset{\overset{O}{\|}}{C}\underset{R_4}{\overset{R_2}{\diagdown}}C=C\underset{R_3}{\overset{}{\diagdown}}$$ (Xb)

Preferably, approximately one mol of a compound of the formula Xa or Xb is employed per mol of one of the compounds of the formulae XI, XII, XIII or XIV. $R_2$, $R_3$ and $R_4$ in the formulae Xa and Xb are as defined above.

When an acid halide of the formula Xa is used, the reaction is carried out in the presence of a base, for example in the presence of a tertiary amine, such as triethylamine, di-isopropyl-ethylamine, N,N-diethylaniline or pyridine; or in the presence of an anhydrous alkali metal carbonate or alkaline earth metal carbonate or alkali metal bicarbonate, such as $MgCO_3$, $NaHCO_3$, $Na_2CO_3$ or $K_2CO_3$. If an acid anhydride of the formula Xb is used in place of the acid chloride, the base can be omitted in some cases.

The organic solvents used in the process variants described above must be inert towards the reactants. Suitable solvents are, for example, aliphatic hydrocarbons, such as hexane or ligroin; aromatic hydrocarbons, such as benzene, toluene or xylene; chlorinated hydrocarbons, such as methylene chloride or chloroform; amides, such as hexamethylenephosphoric acid triamide; or ethers, such as dioxane, 1,2-dimethoxyethane, diethyl ether or tetrahydrofurane.

The temperature of this reaction is preferably $-20°$ to $+120°$ C., but especially $-10°$ C. to $+80°$ C.

The compounds of the formula I in which $R_1$ and $R_3$ together form a group of the formula VIII are prepared by a process analogous to the acid anhydride process described above, approximately one mol of maleic anhydride being reacted with approximately one mol of a compound of the formula XI, in which Y is

$-\overset{|}{N}H$ and $R_5$ and $R_6$ are as defined above. The amide-acid intermediate formed in this reaction is then treated with a water-binding agent, for example acetic anhydride, whereupon water is eliminated while cyclisation is effected.

A further process variant consists in using an ester of the formula Xc

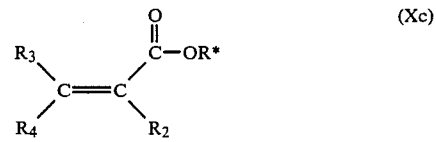 (Xc)

in which $R_2$, $R_3$ and $R_4$ are as defined above and $R^*$ is $C_1$–$C_4$ alkyl, as the reactive derivative of a carboxylic acid of the formula X. The reactants of the formulae XI, XII, XIII or XIV, in which m and n are 1 and the other symbols are as defined above, can be reacted in approximately stoichiometric amounts or with an excess of Xc.

This process variant is a conventional trans-esterification method which takes place at elevated temperature, with or without a solvent and in the presence of a transesterification catalyst, for example of an acid or preferably of a base. The temperature is preferably 20°–170° C. and especially 50°–150° C. If the reaction is carried out in a solvent, the solvent used can be one of those listed above. An ion exchange resin can also be employed as the catalyst. Since the compounds of the formula Xc are liquid compounds, a solvent can be dispensed with in some cases. If necessary, the reactant Xc must be stabilised with one of the known stabilisers, for example hydroquinone, hydroquinone monomethyl ether, 2,6-di-tert.-butyl-p-cresol or another 2,6-di-tert.-butyl-phenyl derivative, or phenothiazine, before the transesterification reaction.

The compounds of the formulae X, Xa, Xb and Xc which are used as starting materials are compounds known to those skilled in the art and can be prepared in a simple manner, if they are not available commercially.

The piperidinyl derivatives used as reactants are also known compounds. The preparation of the compounds of the formula XI has been described, for example, in German Offenlegungsschrift No. 2,352,658 (4-hydroxypiperidines) or in U.S. Pat. No. 3,684,765 (4-aminopiperidines).

The compounds of the formulae XII and XIV can be prepared analogously to the methods described in German Offenlegungsschrift No. 2,227,689.

The preparation of compounds of the formula XIII is known, for example, from German Offenlegungsschrift No. 2,418,540.

The compounds of the formula XI, XII, XIII and XIV which have different substituents in the 2-position and the 6-position of the piperidyl ring can be prepared by reacting a ketone of the formula $CH_3$-CO-$CH_2$-$R_6$ with ammonia. The pyrimidine formed is hydrolysed to an aminoketone of the formula XV, as described in Helv. Chim. Acta 30, 114 (1947).

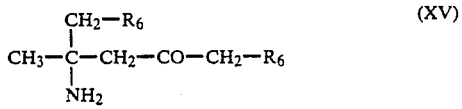

$$CH_3-\underset{\underset{NH_2}{|}}{\overset{\overset{CH_2-R_6}{|}}{C}}-CH_2-CO-CH_2-R_6 \quad (XV)$$

In a second process step, the compounds of the formula XV are reacted with ammonia and a ketone $CH_3$-$CO$-$CH_2$-$R_6$, as has been described, for example, in Monatsh. Chemie 88, 464 (1957) (in the indicated formulae, $R_6$ is as defined above). The compounds of the formulae XI and XII in which $R_5$ is hydrogen can be obtained by hydrolysis from the pyrimidine obtained in this way.

The compounds which carry substituents other than hydrogen in the 1-position and/or the 4-position are prepared analogously to the methods described in the literature references cited above.

The monomers of the formula IX can be polymerised by known methods, which are described, for example, in Houben-Weyl, 14 (1) 1010–1078 (1962).

Suitable reactions for this purpose are, in particular, the reactions known as free radical and ionic homopolymerisation and copolymerisation. The polymerisation is controlled in a known manner by initiators and regulators or chain stoppers. By this means it is possible to obtain polymers of the desired molecular weight. The polymerisation reaction can be carried out in bulk, in solution, in dispersion, in emulsion or in suspension or as a so-called bead polymerisation.

Suitable initiators for free radical homopolymerisation and copolymerisation are, in particular, per-compounds, azo compounds and redox systems. Organic or inorganic per-compounds which are commonly used are, inter alia, hydroperoxides, dialkyl peroxides, diacyl peroxides, per-esters or peroxodisulphates. Examples of per-compounds are hydrogen peroxide, potassium peroxodisulphate, cumene hydroperoxide, di-t-butyl peroxide, ethyl methyl ketone peroxide, cyclohexanone peroxide or dibenzoyl peroxide, which is unsubstituted or substituted by chlorine or bromine. Suitable azo compounds are especially those in which the azo group is bonded to tertiary C atoms on both sides and which also carry nitrile or ester groups in addition to alkyl groups. $\alpha,\alpha'$-Azoisobutyrodinitrile and tert.-butyl perbenzoate are important representatives of this category of initiators. If the polymerisation reaction is initiated by means of a redox system, suitable oxidising agents are organic or inorganic per-compounds and suitable reducing agents are either metal ions of a low valency level or metal-free compounds which can easily be oxidised. Examples of oxidising agents are hydrogen peroxide, peroxodisulphates or diacyl peroxides. Reducing agents which can be used are $Ag^+$, $Fe^{2+}$, $Ti^{2+}$, bisulphite, sulphite, thiosulphate, mercaptans, sulphines, amines, endiols (sugars), benzoin/$Fe^{2+}$ or bisulphite/$Fe^{2+}$. While in the case of the per-compounds and the azo compounds the nature of the initiator has an influence only on the rate of polymerisation, the average degree of polymerisation, the nature of the end groups or the number of branches but not on the polymerisability, not every redox system is suitable for every unsaturated compound.

The molecular weight of the polymer is controlled most simply by means of suitable regulators. Examples are mercaptans, such as n-butylmercaptan or dodecylmercaptan, and other organic sulphur compounds, such as diisopropyl-xanthogen disulphide, and also aliphatic aldehydes and acetals or allyl compounds, such as allyl alcohol. The reaction temperatures are known to those skilled in the art and for free radical polymerisation are $-20°$ C. to $+200°$ C., and preferably $+20°$ C. to $+150°$ C., depending on the nature of the components used. If the polymerisation is carried out ionically, it can be cationic polymerisation, but preferably anionic polymerisation.

Initiators which can be used are metal-organic compounds, such as diethyl-zinc or diisobutyl-zinc, naphthalene-sodium, n-amyl-sodium, cyclopentadienyl-sodium, n-butyl-lithium or triethyl-aluminium. Bases, such as alkali metal hydroxides, alkali metal alcoholates and alkali metal amides, also act as initiators. In place of the regulators used in free radical polymerisation, substances which react with the end of the lengthening chain are employed in the case of ionic polymerisation; such substances include, for example, water, alcohols, acids and amines. The temperature for this reaction variant is from $-100°$ C. to $+200°$ C., preferably $-20°$ C. to $+150°$ C., and the temperature for a particular desired type of polymer is known to those skilled in the art.

It is, furthermore, also possible to use heat, light or other energy-rich radiation as initiators for the polymerisation. The reaction then proceeds by the free radical mechanism. In the case of photo-initiated polymerisation, suitable catalysts are, for example, benzoin ethers, benzil ketals, $\omega$-dialkoxy-acetophenone derivatives or aromatic ketone/amine combinations.

In principle, the methods described are suitable both for homopolymerisation reactions and for copolymerisation reactions. Depending on the choice of the copolymerisation parameters, statistical copolymers or block copolymers are obtained in this way. For the present invention it is essential that the addition of co-monomer components influences only the physical characteristics, such as the softening point, the solubility and the like, but not the usefulness of the polymers as light stabilisers for organic material. Although the copolymerisation of two monomers and the effects associated therewith have been investigated particularly thoroughly and are known to those skilled in the art, it is also useful in certain cases to employ polymers of three or more polymerisable compounds. Such polymers, which are less well known, are described, for example, in G. E. Ham, Copolymerization, High Polymers 18 (1964).

According to the present invention, the compounds of the formula I can be used as stabilisers for plastics in order to protect them against damage by the action of oxygen, heat and light. Examples of such plastics are the polymers listed on pages 12–14 of German Offenlegungsschrift No. 2,456,864.

The stabilising of polyolefines, styrene polymers and polyamides and of polyurethanes is of particular importance, and the compounds of the formula I are outstandingly suitable for this. Examples of such polymers are high density and low density polyethylene, polypropylene, ethylene/propylene copolymers, polystyrene, styrene/butadiene/acrylonitrile terpolymers, polyvinylchloride, polyester-ether, mixtures of polyolefines or of styrene polymers, and polyurethanes based on polyethers or polyesters, in the form of lacquers, filaments, films, sheets, elastomers or foams.

The homopolymeric or copolymeric stabilisers are added to the plastics in a concentration of 0.05 to 5% by weight, calculated relative to the material to be stabilised. Preferably, 0.1 to 2.5% by weight of the compounds, calculated relative to the material to be stabilised, are incorporated into the latter.

Incorporation can be effected after polymerisation, for example by mixing the compounds and, if desired, further additives into the melt by the methods customary in the art, before or during shaping, or by applying the dissolved or dispersed compounds to the polymer, with subsequent evaporation of the solvent if necessary.

The novel compounds can also be added to the plastics to be stabilised in the form of a master batch which contains these compounds, for example in a concentration of 2.5 to 25% by weight.

The invention therefore also relates to the plastics stabilised by the addition of 0.01 to 5% by weight of a compound of the formula I, which plastics can, if desired, contain yet further known and customary additives. The plastics stabilised in this way can be employed in very diverse forms, for example as films, fibres, tapes or profiles or as binders for lacquers, adhesives or putties.

Examples which may be mentioned of further additives, together with which the stabilisers which can be used according to the invention can be employed, are: antioxidants, such as 2,6-dialkylphenols, derivatives of alkylated hydroquinones, hydroxylated thiodiphenyl ethers, alkylidene-bisphenols, O-, N- and S-benzyl compounds, hydroxybenzylated malonates, hydroxybenzyl-aromatic compounds, 2-triazine compounds, amides of β-(3,5-di-tert.-butyl-4-hydroxyphenyl)-propionic acid, esters of β-(3,5-di-tert.-butyl-4-hydroxyphenyl)-propionic acid, esters of β-(5-tert.-butyl-4-hydroxy-3-methylphenyl)-propionic acid, esters of 3,5-di-tert.-butyl-4-hydroxyphenylacetic acid, acylaminophenols, benzylphosphonates, aminoaryl derivatives, UV absorbers and light stabilisers, such as 2-(2'-hydroxyphenyl)benztriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids and acrylates, and, furthermore, nickel compounds, sterically hindered amines, oxalic acid diamides, metal deactivators, phosphites, compounds which destroy peroxide, polyamide stabilisers, basic Co stabilisers, PVC stabilisers, nucleating agents or other additives, for example plasticisers, lubricants, emulsifiers, fillers, carbon black, asbestos, kaolin, talc, glass fibres, pigments, optical brighteners, flame-proofing agents and antistatic agents.

Examples of further additives together with which the stabilisers which can be used according to the invention can be employed are given on pages 18–24 of German Offenlegungsschrift No. 2,427,853.

EXAMPLE 1

25 ml of extremely pure, anhydrous toluene were initially introduced into a reaction vessel provided with a reflux condenser, a dropping funnel, a thermometer, a $N_2$ inlet tube and a stirrer and were heated to 110° C. A solution of 47.8 g of 1,2,2,6,6-pentamethyl-4-methacryloyloxy-piperidine (prepared from 1,2,2,6,6-pentamethyl-4-hydroxy-piperidine and methacrylyl chloride in chloroform in the presence of triethylamine, boiling point: 74°–75° C./0.05 mm Hg) and 380 mg of α,α'-azoisobutyronitrile in 60 ml of pure toluene was added dropwise at a regular rate in the course of 2½ hours to the toluene initially introduced, in a pure nitrogen atmosphere, with stirring. After this solution had been added, the contents of the flask were stirred for a further 10 minutes at 110°–113° C.

70 mg of 1-dodecanethiol in 2 ml of extremely pure toluene were then added as the polymerisation regulator and the polymerisation mixture was stirred for a further 1½ hours at 110°–112° C.

The polymerisation solution, which had cooled to 80° C., was then poured in the course of about 5 minutes into 1.3 liters of methanol at −20° C., with vigorous turbine stirring (Homorex) and the mixture was slowly warmed to room temperature in the course of about 30 minutes. After decanting off the methanol solution, the resinous polymer which had separated out was dissolved in a little dichloromethane and again reprecipitated by pouring the solution into methanol—in the manner described. The poly-1,2,2,6,6-pentamethyl-4-methacryloyloxy-piperidine purified in this way was dried at 80° C. in a vacuum cabinet. The resulting colourless polymer, which can be powdered easily, has a softening point of ~190° C. Molecular weight $(M_n) \approx 12{,}000$.

EXAMPLE 2

10 ml of extremely pure anhydrous toluene were initially introduced into a reaction vessel provided with a reflux condenser, a dropping funnel, a thermometer, a $N_2$ inlet tube and a stirrer and were warmed to 110° C. A solution of 30 g of 1-benzyl-2,2,6,6-tetramethyl-4-acryloyloxy-piperidine, 10.4 g of freshly distilled styrene and 0.20 g of α,α'-azoisobutyronitrile in 25 ml of extremely pure toluene was run dropwise into the reaction vessel in the course of 110 minutes, in a pure $N_2$ atmosphere and with stirring. After this solution had been added, the polymerisation mixture was kept at 110°–112° C. for a further 70 minutes, with stirring. The fairly viscous, water-clear solution which had formed after this time was diluted with 15 ml of toluene and further stirred for a further 60 minutes at 110°–112° C.

The polymerisation solution, which had cooled to about 70° C., was then poured into 800 ml of methanol, which had been pre-cooled to 0° C., with vigorous turbine stirring (Homorex), and as a result the polymer precipitated as a fine white powder. After stirring with the turbine stirrer for a further 30 minutes at room temperature, the copolymer was filtered off, washed well with methanol and dried at 70° C. in a vacuum cabinet. The colourless copolymer obtained in this way has a softening point of 110° C.

1-Benzyl-2,2,6,6-tetramethyl-4-acryloyloxy-piperidine, employed as the monomer component, was obtained by reacting 1-benzyl-2,2,6,6-tetramethyl-4-hydroxypiperidine (melting point: 156°–157° C.) with freshly distilled acrylyl chloride in pure chloroform at 0° to 10° C. in the presence of 1.1 equivalents of anhydrous triethylamine. Recrystallisation from acetonitrile gave the monomer in analytical purity with a melting point of 66°–68° C.

EXAMPLE 3

(A) Analogously to Example 2, 1,2,2,6,6-pentamethyl-4-acryloyloxypiperidine can be obtained from 1,2,2,6,6-pentamethyl-4-hydroxypiperidine and acrylic acid chloride. Boiling Point: 52°–54° C./0.02 mm Hg.

(B) The product described in process 3A can also be obtained by trans-esterification of an acrylic acid ester (for example the methyl or ethyl ester) with 1,2,2,6,6-pentamethyl-4-hydroxypiperidine in the presence of a basic catalyst (suitable catalysts are, for example, tetrabutyl titanate or tetraisopropyl titanate, an alkali metal amide, aluminium isopropoxide or an alkali metal alkoxide), the alcohol which forms being distilled off continuously. After distillation and rectification, the product has the physical data given under A).

EXAMPLES 4 TO 23

The following polymerisable monomers were prepared analogously to the method described in Example 3A or 3B:

| Ex. | Monomer | Physical characteristics | Method according to Ex. |
|---|---|---|---|
| 4 | 1-benzyl-2,2,6,6-tetramethyl-methacryloyloxy-piperidine | boiling point: 175° C./0.03 mm Hg | 1 |
| 5 | 1,2,2,6,6-pentamethyl-4-acrylamido-piperidine | melting point: 133–135° C. | 3A |
| 6 | 1-n-butyl-2,2,6,6-tetra-methyl-4-acryloyloxy-piperidine | boiling point: 96° C./0.1 mm Hg | 3A, 3B |
| 7 | 2,2,6,6-tetramethyl-4-(N-n-butyl)-acrylamido-piperidine | boiling point: 175–180° C./0.05 mm Hg | 3A |
| 8 | 1,2,2,6,6-pentamethyl-4-methacrylamido-piperidine | melting point: 127° C. | 3A |
| 9 | 1-methacryloyloxyethyl-2,2,6,6-tetramethyl-piperidine | boiling point: 130° C./0.04 mm Hg | 3A, 3B |
| 10 | 1-acetyl-2,2,6,6-tetramethyl-4-acryloyloxy-piperidine | melting point: 40–41° C. | 3A, B + Ac$_2$O |
| 11 | 2,2,6,6-tetramethyl-4-acryloyloxy-piperidine | melting point: 55–56° C. | 3A, 3B |
| 12 | 1-allyl-2,2,6,6-tetramethyl-4-acryloyloxy-piperidine | boiling point: 77–78° C./0.04 mm Hg | 3B |
| 13 | 2,5,6-trimethyl-2,6-diethyl-4-acryloyloxy-piperidine | boiling point: 80° C./0.01 mm Hg | 3B |
| 14 | 1,2,5,6-tetramethyl-2,6-diethyl-4-methacryloyloxy-piperidine | boiling point: 110° C./0.01 mm Hg | 3B |
| 15 | 1-acryloyloxyethyl-2,2,6,6-tetramethyl-piperidine | boiling point: 100° C./0.01 mm Hg | 3A, 3B |
| 16 | 1-[2'-acryloyloxy-butyl]-2,2,6,6-tetra-methyl-piperidine | boiling point: 145–150° C./0.04 mm Hg | 3B |
| 17 | 1,3,8-triaza-2,4-dioxo-3-acryloyloxyethyl-7,7,8,9,9-pentamethyl-spiro-[4,5]-decane | melting point: 163–165° C. | 3A, 3B |
| 18 | 1,3,8-triaza-2,4-dioxo-3-n-butyl-7,7,9,9-tetramethyl-8-acryloyl-oxyethyl-spiro-[4,5]-decane | melting point: 153–155° C. | 3A, 3B |
| 19 | 1,3,8-triaza-2,4-dioxo-3-n-octyl-7,7,9,9-tetramethyl-8-acryloyl-oxyethyl-spiro-[4,5]-decane | melting point: 97–98° C. | 3A, 3B |
| 20 | 1,2,2,6,6-pentamethyl-4-(N-n-propyl)-acryl-amido-piperidine | melting point: 43–44° C. | 3A |
| 21 | 1-benzyl-2,2,6,6-tetramethyl-4-(N-n-butyl)-acrylamido-piperidine | melting point: 108–110° C. | 3A |
| 22 | 2,5,6-trimethyl-2,6-diethyl-4-(N-methyl)-acrylamido-piperidine | boiling point: 110° C./0.001 mm Hg | 3A |

-continued

| Ex. | Monomer | Physical characteristics | Method according to Ex. |
|---|---|---|---|
| 23 | 1,2,2,6,6-pentamethyl-4-maleimido-piperidine (prepared from 1,2,2,6,6-pentamethyl-4-aminopiperidine and maleimide) | melting point: 116–117° C. | |
| 24 | 2,2,6,6-tetramethyl-4-acryl-amidopiperidine | melting point: 121–122° C. | 3A |
| 25 | 1-acryloyl-2,2,6,6-tetramethylpiperidine | melting point: 34–34,5° C. | 3A |
| 26 | 1-(3'-phenyloxy-2'-acryloyloxypropyl)-2,2,6,6-tetramethyl-piperidine | boiling point: 195–200° C. 0,05 mmHg | 3A |
| 27 | 1-oxyl-2,2,6,6-tetramethyl-4-acryloyloxy-piperidine | melting point: 101–102° C. | 3A |
| 28 | 1,3,8-triaza-2,4-dioxo-3-n-dodecyl-7,7,9,9-tetramethyl-8-acryloyl-spiro[4,5]decane | melting point: 60–62° C. | 3A, 3B |
| 29 | 1,3,8-triaza-2,4-dioxo-3-methacryloyloxypropyl-7,7,9,9-tetramethyl-8-oxyl-spiro-[4,5]decane | melting point: 113–114° C. | 3A, 3B |
| 30 | 1,3,8-triaza-2,4-dioxo-3-methacryloyloxypropyl-7,7,9,9-tetramethyl-spiro[4,5]decane | melting point: 108–109° C. | 3A, 3B |
| 31 | 1-oxyl-2,2,6,6-tetramethyl-4-acrylamido-piperidine | melting point: 149–150° C. | 3A |
| 32 | 2,2,6,6-tetramethyl-4-acrylamido-piperidine | melting point: 122–123,5° C. | 3A |

EXAMPLE 33

445 g of distilled 4-acryloyloxy-1,2,2,6,6-pentamethyl-piperidine and 100 mg of dodecylmercaptan in 1,500 ml of pure benzene were initially introduced into a reaction vessel provided with a reflux condenser, a dropping funnel, a thermometer, a gas inlet tube and an anchor stirrer (after the reaction vessel had been flushed completely with argon) and the solution was warmed rapidly to 76° C. A solution of 1.5 g of α,α'-azoisobutyronitrile (dissolved in 50 ml of pure benzene) was added dropwise at this temperature in the course of 45 minutes at a very regular rate, with stirring, and during the addition the internal temperature rose to a maximum of 80° and the heat of polymerisation was removed via the reflux condenser. The polymerisation solution was then stirred for a further 22 hours at 75°–76° C.

About 1,000 ml of benzene were then distilled off from the reaction solution, which was now somewhat viscous but still completely colourless, in a rotary evaporator under a waterpump vacuum. The concentrated viscous polymer solution was now poured slowly into 3.6 liters of methanol at 0° C., with vigorous stirring with a turbine stirrer; at this temperature, only a slight polymer precipitate forms initially. The precipitation was brought to completion by slowly warming the methanol solution to 25°–28° C. After stirring for about 30 minutes with a turbine stirrer, the supernatant methanol was decanted off and the polymer precipitate was repeatedly washed with a little methanol, the methanol was again decanted off and the sediment was finally dissolved in methylene chloride and the solvent was removed as completely as possible from the solution in a rotary evaporator under a waterpump vacuum. The powdery-brittle polymer was then dried completely in a vacuum drying cabinet at 80°. The readily pulverisable colourless polymeric 4-acryloyloxy-1,2,2,6,6-pentamethyl-piperidine thus obtained has a softening point of ~115° C. and an average molecular weight ($\overline{M}_n$) of 29,000.

| Example | Monomer (Example No.) | Polymer/Copolymer |
|---|---|---|
| 34 | 9 | s.p. : ~145° C. $\overline{M}n$ : ~7,000 analogous to Example 1 |
| 35 | 15 | s.p. : ~70° C. $\overline{M}n$ : ~4,000 analogous to Example 1 R: — |
| 36 | 16 | s.p. : ~85° C. $\overline{M}n$ : 3,000 analogous to Example 33 |
| 37 | 17 | s.p. : ~165° C. $\overline{M}n$ : ~14,000 analogous to Example 33 R: — |
| 38 | 18 | s.p. : ~160° C. $\overline{M}n$ : ~7,000 analogous to Example 33 |
| 39 | 19 | s.p. : ~125° C. $\overline{M}n$ : ~8,200 analogous to Example 33 R: — |
| 40 | 22 | s.p. : ~220° C. $\overline{M}n$ : ~6,000 analogous to Example 33 R: — |
| 41 | 21 | s.p. : ~220° C. $\overline{M}n$ : ~12,600 analogous to Example 33 R: — |
| 42 | 1 part of 3 + 1 part of styrene | s.p. : ~110° C. $\overline{M}n$ : ~6,700 |
| 43 | 2 parts of 3 + 1 part of styrene | s.p. : 115–120° C. $\overline{M}n$ : ~14,400 |
| 44 | 1 part of 1 + 1 part of styrene | s.p. : 155–160° C. $\overline{M}n$ : ~9,700 |
| 45 | 0.9 part of 2 + 1 part of styrene | s.p. : 110–115° C. $\overline{M}n$ : ~2,200 |
| 46 | 1 part of 2 + 1 part of styrene | s.p. : 110–115° C. $\overline{M}n$ : ~3,000 |
| 47 | 3 parts of 3 + 2 parts of ethyl acrylate | s.p. : ~80° C. $\overline{M}n$ : ~30,000 |
| 48 | 2 parts of 3 + 1 part of t.-butyl acrylate | s.p. : ~105° C. $\overline{M}n$ : ~150,000 |
| 49 | 2 parts of 3 + 1 part of ethyl acrylate | s.p. : ~96° C. $\overline{M}n$ : ~33,000 |
| 50 | 5 parts of 1 + 1 part of ethyl acrylate | s.p. : ~165° C. $\overline{M}n$ : ~19,600 |
| 51 | 1 part of 1 + 1 part of ethyl methacrylate | s.p. : ~145° C. $\overline{M}n$ : ~6,500 |
| 52 | 6 parts of 3 + 5 parts of acrylonitrile | s.p. : ~120° C. $\overline{M}n$ : ~29,800 |
| 53 | 1 part of 3 + 1 part of N-vinylpyrrolidone-2 | s.p. : 145–150° C. $\overline{M}n$ : ~8,200 |
| 54 | 2 parts of 3 + 1 part of N-vinylpyrrolidone-2 | s.p. : 120–125° C. $\overline{M}n$ : 15,300 |
| 55 | 2 parts of 2 + 1 part of N-vinylpyrrolidone-2 | s.p. : 155–160° C. $\overline{M}n$ : 94,300 |
| 56 | 1 part of 1 + 1 part of vinyl acetate | s.p. : ~165° C. $\overline{M}n$ : ~88,000 |
| 57 | 1 part of 3 + 1 part of t.-butyl acrylate | s.p. : ~130° C. $\overline{M}n$ : 20,900 |
| | + 1 part of N-vinylpyrrolidone-2 | |
| 58 | 2 parts of 3 + 1 part of N-vinylpyrrolidone-2 | |
| 59 | 2 parts of 3 + 1 part of 2,3-epoxypropyl acrylate | s.p. : ~80° C. $\overline{M}n$ : 12,600 |
| 60 | 3 parts of 3 + 1 part of 2-hydroxyethyl acrylate | s.p. : ~110° C. $\overline{M}n$ : 6,500 |
| 61 | 3 parts of 3 + 1 part of acrylic acid | |
| 62 | 2 parts of 3 + 1 part of acrylic acid t.-butylamide | s.p. : ~115° C. $\overline{M}n$ : ~9,400 |
| 63 | 3 parts of 3 + 2 parts of maleimide | s.p. : ~210° C. |
| 64 | 1 part of 3 + 1 part of N-ethyl-maleimide | s.p. : ~145° C. $\overline{M}n$ : ~15,700 |
| 65 | 1 part of 3 + 0.85 part of N-benzyl-maleimide | s.p. : 135–138° C. $\overline{M}n$ : ~8,400 |
| 66 | 1 part of 3 + 1 part of N-phenyl-maleimide | s.p. : ~205° C. $\overline{M}n$ : ~14,500 |
| 67 | 1 part of 3 + 1 part of 23 | s.p. : 200–205° C. $\overline{M}n$ : ~20,000 |
| 68 | 1 part of 23 + 1 part of ethyl acrylate | s.p. : ~155° C. $\overline{M}n$ : ~10,200 |
| 69 | 6 parts of 3 + 5 parts of 23 | s.p. : ~205° C. $\overline{M}n$ : 14,600 |
| 70 | 6 parts of 3 + 5 parts of N-benzyl-maleimide | s.p. : ~165° C. $\overline{M}n$ : ~15,500 |
| 71 | 1 part of 3 + 1 part of 1 | s.p. : ~165° C. $\overline{M}n$ : ~28,900 |
| 72 | 1 part of 3 + 1 part of 20 | s.p. : ~150° C. $\overline{M}n$ : ~11,500 |
| 73 | 26 | s.p. : ~100° C. $\overline{M}n$ : ~5,000 |
| 74 | 25 | s.p. : ~260° C. $\overline{M}n$ : 12,500 |
| 75 | 29 | s.p. : ~165° C. $\overline{M}n$ : ~50,000 |
| 76 | 30 | s.p. : ~160° C. $\overline{M}n$ : ~13,100 |
| 77 | 1 part of 27 + 10 parts of methylmethacrylate | s.p. : ~130°° C. $\overline{M}n$ : ~50,500 |
| 78 | 1 part of 11 + 10 parts of methylmethacrylate | s.p. : ~125° C. $\overline{M}n$ : ~13,900 |
| 79 | 1 part of 3 + 1 part of methylmethacrylate | s.p. : ~105° C. $\overline{M}n$ : 32,400 |
| 80 | 28 | s.p. : >250° C. $\overline{M}n$ : ~45,000 |
| 81 | 1 part of 3 + 1 part of ethylene | $\overline{M}n$ : ~36,000 |
| 82 | 1 part of 11 + 5,5 parts of ethylene | s.p. : 50–60° C. |
| 83 | 1 part of 11 + 16,3 parts of ethylene | $\overline{M}n$: ~33,600 |
| 84 | 1 part of 3 + 1 part of N-cyclohexyl-maleimide | s.p. : ~180° C. $\overline{M}n$ : ~9,800 |
| 85 | 1 part of 12 + 16 parts of ethylene | s.p. : ~65° C. $\overline{M}n$ : ~6,000 |
| 86 | 1 part of 3 + 16 parts of ethylene | s.p. : ~55° C. $\overline{M}n$ : ~6,000 |
| 87 | 1 part of 3 + 9 parts of N-vinylpyrrolidone | s.p. : ~118° C. $\overline{M}n$ : 16,600 |

EXAMPLE 88

Stabilisation of polypropylene against light 100 parts of polypropylene powder (Moplen, fibre grade, marketed by Montedison), 0.2 part of β-(3,5-di-tert-butyl-4-hydroxyphenyl)octadecylpropionate and 0.25 part of a stabiliser of the following table are homogenised for 10 minutes at 200° C. in a Brabender plastograph. The resulting mass is removed from the kneader as quickly as possible and pressed to a sheet having a thickness of 2 to 3 mm in a toggle press. A portion of this sheet is cut out and pressed between two high-gloss aluminium sheets with a hand-operated hydraulic laboratory press for 6 minutes at 260° c. and under a pressure of 12 tons to a sheet having a thickness of 0.1 mm which is immediately chilled in water. Sections each measuring 60×44 mm are then punched out of this sheet and exposed in a xenotest 1200 These blanks are taken out of the exposure apparatus at regular intervals and tested for their carbonyl content in an IR spectrophotometer. The increase of the carbonyl extinction of 5.85μ during the exposure is an index of the photooxidative degradation of the polymer (see L. Blaban et al., J. Polymer Sci, Part C; 22, 1059–1071 (1969) and, as previous experience has shown, is allied to a decrease in the mechanical properties of the polymer.

The time taken until a carbonyl extinction of about 0.3 is attained, at which the comparison sheet is brittle, serves as index of the protective action.

The protective action of the stabilisers of the invention is evident from the following table:

| Additive | Exposure time in a xenotest 1200 until a carbonyl extinction of 0.3 has been detected |
|---|---|
| none | 710 |
| 41 | 1365 |
| 1 | 2340 |
| 40 | 1225 |
| 37 | 2450 |
| 39 | 4750 |
| 35 | 7000 |
| 34 | 6270 |
| 36 | 4585 |
| 63 | 2285 |
| 65 | 2180 |
| 66 | 1800 |
| 64 | 2345 |
| 47 | 1740 |
| 49 | 2080 |
| 50 | 2150 |
| 51 | 3130 |
| 59 | 2375 |
| 60 | 3380 |
| 62 | 2530 |
| 71 | 2660 |
| 67 | 2915 |
| 72 | 3305 |
| 69 | 2060 |
| 43 | 2240 |
| 42 | 2180 |
| 54 | 2430 |
| 55 | 2660 |
| 44 | 2115 |
| 51 | 2990 |
| 68 | 2545 |

EXAMPLE 89

Light stabilising action in PP fibres 1,000 parts of unstabilised polypropylene powder (melt index ~18) are mixed in a drum mixer with 1 part of pentaerythrityl-tetrakis[3-(3,5-di-tert.-butyl-4-hydroxyphenyl)-propionate] and with the light stabilisers indicated in the table and the mixture is then extruded in an extruder at 220° C. and granulated. The resulting granules are spun in a laboratory melt-spinning installation at a maximum temperature of 270° C. and a speed of 300 m/minute to a 570/12 denier multifilament. This is stretched and twisted by means of a stretch/twisting machine. The stretching ratio is 1:5.6 and the twist number 15/meter, so that finally 120/12 denier multifilaments are obtained. These multifilaments are mounted on white card and exposed in the Xenotest 1,200.

The exposure time taken to reach a loss in tear strength of 50% is taken as a measure of the protective action.

The results are summarised in the table.

| Additive No. | parts | Hours taken to reach 50% residual tear strength |
|---|---|---|
| none | — | 215 |
| 46 | 3 | 500 |
| 43 | 3 | 1500 |
| 42 | 3 | 1350 |
| 53 | 3 | 2200 |
| 66 | 3 | 1200 |
| 47 | 3 | 1350 |
| 49 | 3 | 1425 |
| 52 | 3 | 1900 |
| 51 | 3 | 1800 |

What is claimed is:

1. A copolymer of a compound which carries N-heterocyclic rings in a side position and has the recurring structural unit of the formula I

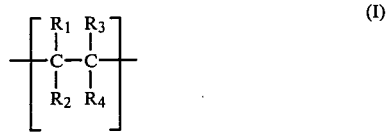

(I)

in which $R_1$ is a group, containing an N-heterocyclic ring, of the formulae II, III, IV and V

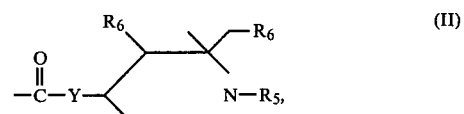

(II)

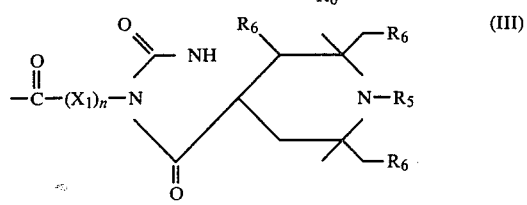

(III)

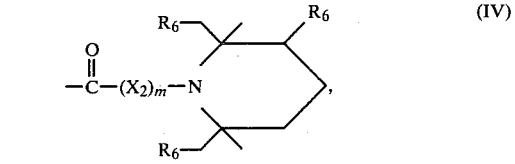

(IV)

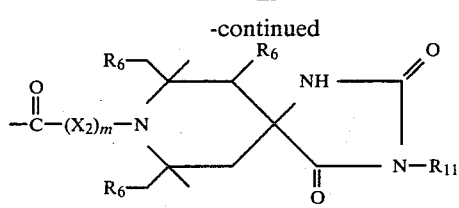

in which $R_5$ is hydrogen, oxyl, $C_1$-$C_{18}$ alkyl, 2-hydroxyethyl, 2-hydroxypropyl, $C_3$-$C_8$ alkenyl, $C_3$-$C_6$ alkynyl, $C_7$-$C_{12}$ aralkyl, $C_2$-$C_{21}$ alkoxyalkyl, an aliphatic acyl group having 1-4 C atoms or one of the groups —$CH_2COOR_7$ or —$COOR_8$, in which $R_7$ is $C_1$-$C_{12}$ alkyl, $C_3$-$C_8$ alkenyl, phenyl, $C_7$-$C_8$ aralkyl or cyclohexyl and $R_8$ is $C_1$-$C_{12}$ alkyl, phenyl, benzyl or cyclohexyl, and $R_6$ is hydrogen or $C_1$-$C_4$ alkyl and Y is —O— or

in which $R_9$ is hydrogen, $C_1$-$C_{12}$ alkyl, $C_7$-$C_{12}$ aralkyl or cyclohexyl, and $X_1$ is a group of the formula —O—$CH(R_{10})$—$CH_2$— (VI) or denotes —O—$CH_2$—$CH_2$—$CH_2$—, in which $R_{10}$ is hydrogen, methyl, ethyl, phenoxymethyl or phenyl, and n is 0 or 1, and $X_2$ is a group of the formula VI, in which $R_{10}$ is as defined above, or a group of the formula —O—$CH_2$—$CH(OH)$—$CH_2$— (VII), and m is 0 or 1, and $R_{11}$ is $C_1$-$C_{18}$ alkyl or is cyclohexyl, phenyl or benzyl which are unsubstituted or substituted by $C_1$-$C_4$ alkyl or $C_1$-$C_4$ alkoxy, and $R_2$ is hydrogen or $C_1$-$C_4$ alkyl, and, if $R_2$ and $R_4$ are hydrogen, $R_1$ and $R_3$ together form a group of the formula VIII

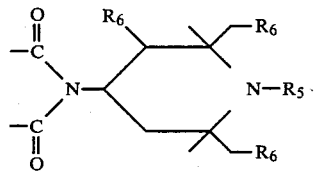

in which $R_5$ and $R_6$ are as defined above and $R_3$ is hydrogen or $C_1$-$C_2$ alkyl and $R_4$ is hydrogen or methyl, with a compound containing at least one polymerisable double bond, the molar ratio of the component of the formula I to the co-component being up to 1:10.

2. A copolymer of a compound according to claim 1, of the formula I, in which $R_1$ is a group of the formulae II, III, IV or V, in which $R_5$ is hydrogen, $C_1$-$C_{12}$ alkyl, 2-hydroxyethyl, 2-hydroxypropyl, $C_3$-$C_5$ alkenyl, propargyl, $C_7$-$C_8$ aralkyl, acetyl or $C_2$-$C_{10}$ alkoxyalkyl and $R_6$ is hydrogen or methyl and Y is —O— or

in which $R_9$ is hydrogen, $C_1$-$C_{12}$ alkyl or benzyl, and $X_1$ is a group of the formula VI or denotes —O—$CH_2$—$CH_2$—$CH_2$—, in which $R_{10}$ is hydrogen or methyl, and n is 0 or 1, and $X_2$ is a group of the formulae VI or VII, in which $R_{10}$ is as defined above, and m is 0 or 1, and $R_{11}$ is $C_1$-$C_{12}$ alkyl or benzyl, and $R_2$ is hydrogen or $C_1$-$C_2$ alkyl, or, if $R_2$ and $R_4$ are hydrogen, $R_1$ and $R_3$ together form a group of the formula VIII, in which $R_5$ and $R_6$ are as defined above, and $R_3$ is hydrogen or $C_1$-$C_2$ alkyl and $R_4$ is hydrogen or methyl, with a compound containing at least one polymerisable double bond.

3. A copolymer of a compound according to claim 1, of the formula I, in which $R_1$ is a group of the formula II or IV, in which $R_5$ is hydrogen, $C_1$-$C_8$ alkyl, benzyl or acetyl and $R_6$ is hydrogen or methyl and Y is —O— or

in which $R_9$ is hydrogen or $C_1$-$C_8$ alkyl, and $X_2$ is a group of the formula IV or VII, in which $R_{10}$ is hydrogen, methyl or ethyl, and m is 0 or 1, and $R_2$ is hydrogen or methyl or, if $R_2$ and $R_4$ are hydrogen, $R_1$ and $R_3$ together are a group of the formula VIII, in which $R_5$ and $R_6$ are as defined above, and $R_3$ is hydrogen or methyl and $R_4$ is hydrogen, with a compound containing at least one polymerisable double bond.

4. A copolymer of a compound according to claim 1, of the formula I, in which $R_1$ is a group of the formula II or IV, in which $R_5$ is hydrogen, $C_1$-$C_4$ alkyl, benzyl or acetyl and $R_6$ is hydrogen and Y is —O— or

in which $R_9$ is hydrogen or $C_1$-$C_4$ alkyl, and $X_2$ is a group of the formula VI or VII, in which $R_{10}$ is hydrogen or methyl, and m is 0 or 1, and $R_2$ and $R_3$ independently of one another are hydrogen or methyl and $R_4$ is hydrogen, with styrene, acrylonitrile, an acrylate or a methacrylate, a vinyl ester, a vinyl ether or an acrylamide or methacrylamide.

5. A copolymer of a compound according to claim 1, of the formula I, in which $R_1$ is a group of the formula II or IV, in which $R_5$ is hydrogen, methyl or acetyl and $R_6$ is hydrogen and Y is —O— or

in which $R_9$ is hydrogen or $C_1$-$C_4$ alkyl, and $X_2$ is group of the formula VI or VII, in which $R_{10}$ is hydrogen, and m is 0 or 1, and $R_3$ and $R_4$ are hydrogen and $R_2$ is hydrogen or methyl, with styrene, acrylonitrile, an acrylate or methacrylate, a vinyl ester, a vinyl ether or an acrylamide or methacrylamide.

6. A copolymer of a compound of the formula I according to claim 1, with a methyl, ethyl or butyl acrylate or methacrylate, a maleimide, N-vinyl-pyrrolidone or a glycidyl acrylate, the molar ratio of the component of the formula I to the co-component being up to 1:10.

7. A homopolymeric compound with the recurring structural unit of the formula I, according to claim 1, in which $R_1$ is a group of the formula III, IV or V and the other symbols are as defined in claim 1.

8. A homopolymeric compound according to claim 1, wherein $R_1$ and $R_3$ together form a group of the formula VIII.

9. A homopolymeric compound according to claim 7, wherein $R_1$ is a group of the formula IV.

10. A homopolymeric compound according to claim 7, wherein $R_1$ is a group of the formula V.

11. A homopolymeric or copolymeric compound according to claim 1, of the formula I, in which $R_1$ and $R_3$ together are a grouping of the formula VIII.

12. A copolymeric compound according to claim 11.

* * * * *